US011219220B2

United States Patent
Yin et al.

(10) Patent No.: US 11,219,220 B2
(45) Date of Patent: Jan. 11, 2022

(54) **PREPARATION METHOD OF *BEAUVERIA BASSIANA* MICROSCLEROTIUM AND FORMULATION THEREOF, APPLICATION OF FORMULATION THEREOF**

(71) Applicant: CHONGQING UNIVERSITY, Chongqing (CN)

(72) Inventors: Youping Yin, Chongqing (CN); Zhongkang Wang, Chongqing (CN)

(73) Assignee: CHONGQING UNIVERSITY, Chongqing (CN)

( * ) Notice: Subject to any disclaimer, the term of this patent is extended or adjusted under 35 U.S.C. 154(b) by 134 days.

(21) Appl. No.: 16/623,010

(22) PCT Filed: May 6, 2019

(86) PCT No.: PCT/CN2019/085650
§ 371 (c)(1),
(2) Date: Dec. 16, 2019

(87) PCT Pub. No.: WO2020/038020
PCT Pub. Date: Feb. 27, 2020

(65) Prior Publication Data
US 2021/0007362 A1    Jan. 14, 2021

(30) Foreign Application Priority Data

Aug. 23, 2018   (CN) .......................... 201810968356.2

(51) Int. Cl.
| | |
|---|---|
| *C12N 3/00* | (2006.01) |
| *A01N 63/30* | (2020.01) |
| *C12N 1/14* | (2006.01) |

(52) U.S. Cl.
CPC .............. *A01N 63/30* (2020.01); *C12N 1/14* (2013.01); *C12N 3/00* (2013.01)

(58) Field of Classification Search
CPC ............. C12N 3/00; C12N 1/14; A01N 63/30
See application file for complete search history.

(56) References Cited

U.S. PATENT DOCUMENTS

2002/0146444 A1   10/2002 Bradley et al.
2016/0183532 A1*   6/2016 Taghavi et al. ........ A01N 63/00

FOREIGN PATENT DOCUMENTS

| CN | 101245319 A | 8/2008 |
|---|---|---|
| CN | 102206587 A | 10/2011 |
| CN | 104357338 A | 2/2015 |
| CN | 105695344 A | 6/2016 |
| CN | 108949588 A | 12/2018 |

OTHER PUBLICATIONS

Wang Haihong et. al., 2011—Corresponding to CN102206587A cited in applicant's IDS dated Apr. 19, 2021—"Culture method of sclerotium of *Beauveria bassiana* and application thereof", English machine-translation (total pp. 1-16). (Year: 2011).*

Yuan et al., "Screening of Higher Virulent Fungal Strain against Delia antigua", Chinese Journal of Biological Control, Jan. 2016, vol. 32, No. 2, pp. 165-171 (total pp. 1-7 with English ABSTRACT). (Year: 2016).*

Wang Jinyao et al., 2008—Corresponding to CN101245319A cited in applicant's IDS dated Apr. 19, 2021, "Macrophomina *Beauveria bassiana* HFW-05 bacterial strain and uses thereof", English machine-translation (total pp. 1-14). (Year: 2008).*

First Office Action dated Apr. 3, 2020 issued in Chinese Patent Application No. 201810968356.2.

\* cited by examiner

*Primary Examiner* — Satyendra K Singh
(74) *Attorney, Agent, or Firm* — Troutman Pepper Hamilton Sanders LLP; Christopher C. Close, Jr.

(57) ABSTRACT

The present invention provides a preparation method of *Beauveria bassiana* (Bals.) Vuill microsclerotium and a formulation thereof, and an application of the formulation thereof, belonging to the technical field of microsclerotium formulation preparation; the *Beauveria bassiana* microsclerotium formulation is prepared by the following steps of: 1) mixing conidia of *Beauveria bassiana* with Tween® 20 aqueous solution to obtain spore suspension; 2) inoculating the prepared spore suspension into a liquid induction medium for induction culture to obtain microsclerotium; 3) mixing the prepared microsclerotium with a padding for drying to obtain dried microsclerotium; 4) mixing the prepared dried microsclerotium with an auxiliary to obtain a microsclerotium formulation. The *Beauveria bassiana* microsclerotium formulation produced by the method has low production cost, strong product tolerance and good insecticidal activity, moreover, after rehydrated, the formulation may rapidly germinate hyphae and produce spores to infect pests.

5 Claims, No Drawings

PREPARATION METHOD OF *BEAUVERIA BASSIANA* MICROSCLEROTIUM AND FORMULATION THEREOF, APPLICATION OF FORMULATION THEREOF

The application claims the priority of a Chinese patent application 201810968356.2 filed to Patent Office of the People's Republic of China on Aug. 23, 2018, and entitled "preparation method of *Beauveria bassiana* microsclerotium and formulation thereof, application of formulation thereof", the contents of which are hereby incorporated by reference into the present application.

TECHNICAL FIELD

The present invention relates to the technical field of the microsclerotium formulation preparation, and in particular to a preparation method and an application of *Beauveria bassiana* microsclerotium.

DEPOSIT OF *BEAUVERIA BASSIANA* STRAIN CQBb119 MICROORGANISMS

Deposit Institution: China General Microbiological Culture Collection Center (CGMCC)
Accession Number: CFMCC NO: 15987
Deposit Date: Jun. 27, 2018

BACKGROUND

With the advancement of China's ecological civilization construction, the decrease of chemical pesticide utilization has been an irresistible trend, and eco-friendly biological control technologies will attract more attention. *Beauveria bassiana* is a kind of broad-spectrum pathogenic fungus and has good insecticidal activity to various kinds of *Lepidoptera*, Coleoptera and Hemiptera pests, and it is widely applied in the biological control of various domestic and overseas pests, such as *Agrotis ipsilon* and pine moth.

At present, usually conidium is the active ingredient of the practical *Beauveria bassiana* formulation, and the conidium is obtained by liquid-solid phase fermentation, but the method has long fermentation period, low production efficiency, high production cost, moreover the product has limited tolerance to adverse environment and short shelf life, therefore, it is limited in practical production and application to a large extent.

SUMMARY

The objective of the present invention is to provide a preparation method of *Beauveria bassiana* microsclerotium and formulation thereof, an application of the formulation thereof; the *Beauveria bassiana* microsclerotium formulation has low production cost, strong product tolerance and good insecticidal activity, moreover, after rehydrated, the formulation may rapidly germinate hyphae and produce spores to infect pests.

To achieve the above purpose, the present invention provides the following technical solution.

The present invention provides a preparation method of *Beauveria bassiana* microsclerotium, including the following steps of:

1) mixing conidia of *Beauveria bassiana* with Tween® 20 aqueous solution to obtain spore suspension;

2) inoculating the spore suspension in step 1) into a liquid induction medium for induction culture to obtain the microsclerotium; where, the volume percent of Tweenx 20 in the Tweenx 20 aqueous solution in step 1) was 0.03%-0.1%;

with water as solvent, per liter of the liquid induction medium in step 2) includes the following ingredients: 2-6 g $KH_2PO_4$, 0.3-0.9 g $MgSO_4 \cdot 7H_2O$, 0.4-1.2 g $NaNO_3$, 0.2-0.6 g $CuSO_4$, 1.5-4.5 g yeast powder, 1-3 g peptone; 10-30 g sucrose, 2.5 mL-7.5 mL Tween® 20 and 1000 mL water, pH=6.0-7.5.

Preferably, the *Beauveria bassiana* strain is CQBb119 and the accession number is CGMCC NO:15987.

Preferably, the spore content of the spore suspension in step 1) is $2.8 \times 10^6 \text{-} 3.2 \times 10^6$ spores/mL.

Preferably, the volume ratio of the inoculated spore suspension in step 2) to the liquid induction medium is 1:(10-20).

Preferably, the induction culture temperature in step 2) is 23-31° C.; the induction culture time is 5-6 d; the oscillation or stirring frequency of the induction culture is 50-250 rpm.

The present invention provides a preparation method of a *Beauveria bassiana* microsclerotium formulation, including the following steps of:

A) mixing a microsclerotium prepared by the method according to any one of claims 1-5 with a padding for drying to obtain dried microsclerotium;

B) mixing the dried microsclerotium in step A) with an auxiliary to obtain the microsclerotium formulation.

Preferably, the dosage form of the *Beauveria bassiana* microsclerotium formulation is granule.

Preferably, the padding in step A) is one or more of diatomite, starch and cyclodextrin; the volume ratio of the microsclerotium to the padding is 1:(2-4).

Preferably, the auxiliary in step B) is sucrose ester; the mass ratio of the dried microsclerotium to the sucrose ester is 1000:1-200:1.

The present invention provides an application of the *Beauveria bassiana* microsclerotium formulation obtained by the above preparation method in controlling various pests.

Beneficial Effects of the Present Invention

1. *Beauveria bassiana* with accession number of CGMCC NO:15987 is taken in the present invention, and the strain has high insecticidal activity and broad-spectrum insecticidal efficacy, especially for *Homoptera* pests with piercing-sucking mouthparts, *Lepidoptera agrotis* ypsilon and Diptera larva controlled by conventional insecticides difficultly. Moreover, liquid fermentation is firstly applied in the present application to induce a large number of *Beauveria bassiana* microsclerotia.

2. The *Beauveria bassiana* microsclerotium formulation prepared by the method of the present application may adapt 35-40° C., strong ultraviolet ray and other adverse environment, moreover the product has good stress resistance and 1-2-year shelf life.

3. The *Beauveria bassiana* microsclerotium formulation produced by the present invention has good insecticidal activity, and may rapidly germinate hyphae and produce spores to infect pests after rehydrated; LT50 (half lethal time: time that 50% pests die after inoculation) is 5.3 d-7.2 d, therefore, it may substitutes conidium as an active ingredient of insecticidal fungi.

4. The present invention has simple fermentation process, conventional raw materials, strong operability of the culture solution and fermentation process, good repeatability, capable of achieving full-auto production; moreover, the present invention has short fermentation period, only for 5-6 d, while the conventional liquid-solid phase fermentation consumes 20-25 d.

5. The production cost of the present invention decreases 1/2 above relative to the fermentation cost of conidium, and moreover there is no waste in production.

Description of Biological Preservation

*Beauveria bassiana* (Bals.) Vuill was preserved in China General Microbiological Culture Collection Center (CGMCC) (address: Institute of Microbiology of Chinese Academy of Sciences, No. 3, Yard 1, West Beichen Road, Chaoyang District, Beijing) on Jun. 27, 2018 with the accession number of CGMCC NO: 15987.

DETAILED DESCRIPTION

The present invention provides a preparation method of a *Beauveria bassiana* microsclerotium, and the strain is CQBb119 and the accession number: CGMCC NO:15987.

In the present invention, the *Beauveria bassiana* strain is inoculated into a PDA solid medium for culture and collected to obtain conidia; the diameter of the PDA plate is preferably 90 mm; the culture time of the strain is preferably 10-12 d; the culture temperature of the strain is preferably 23-25° C.; the collection method is to scrape conidia on the surface of the plate after hyphae grow all over the plate and produce spores.

In the present invention, the collected conidia are mixed with Tweenx 20 aqueous solution to obtain a spore suspension; content of Tween® 20 in the Tween® 20 aqueous solution is 0.03%-0.1%, preferably 0.05%; water in the Tween® 20 aqueous solution is sterile water; the final concentration of the spore suspension is $2.8 \times 10^6 - 3.2 \times 10^6$ spores/mL, preferably $3.0 \times 10^6$ spores/mL, and the mixing is implemented in aseptic conditions.

In the present invention, the obtained spore suspension is inoculated into a liquid induction medium for induction culture to obtain microsclerotium; the liquid induction medium includes the following components: counted by 1 L, 2-6 g $KH_2PO_4$, 0.3-0.9 g $MgSO_4 \cdot 7H_2O$, 0.4-1.2 g $NaNO_3$, 0.2-0.6 g $CuSO_4$; 1.5-4.5 g yeast powder, 1-3 g peptone, 10-30 g sucrose, 0.25-0.75 mL Tween® 20 and 1000 mL water, pH=6.0-7.5; preferably, counted by 1 L, 3-5 g $KH_2PO_4$, 0.5-0.7 g $MgSO_4 \cdot 7H_2O$, 0.8-1.0 g $NaNO_3$, 0.3-0.5 g $CuSO_4$; 2.5-3.5 g yeast powder, 1.5-2.5 g peptone, 15-25 g sucrose, 0.35-0.65 mL Tween® 20 and 1000 mL water, pH=6.5-7.2; more preferably, counted by 1 L, 4 g $KH_2PO_4$, 0.6 g $MgSO_4 \cdot 7H_2O$, 0.9 g $NaNO_3$, 0.4 g $CuSO_4$; 3 g yeast powder, 2 g peptone, 20 g sucrose, 0.5 mL Tween® 20 and 1000 mL water, pH=7.0. In the present invention, the volume ratio of the inoculated spore suspension to the liquid induction medium is 1: (10-20), preferably 1:(12-18), more preferably 1: 15; the final content of the inoculated spores is preferably $\geq 1.25 \times 10^5$ spores/L. In the present invention, the temperature of the induction culture is 23-31° C., preferably 25-29° C., more preferably 28° C.; the time of the induction culture is 5-6 d, preferably 5.5 d; the oscillation frequency of the induction culture is 50-250 rpm, in embodiments of the present invention, preferably, the oscillation frequency after inoculated within 24 h is preferably 50-100 rpm, more preferably 100 rpm; the oscillation frequency after inoculated within 24 h is preferably 110-200 rpm, more preferably 180 rpm.

The present invention provides a preparation method of the *Beauveria bassiana* microsclerotium formulation, and the *Beauveria bassiana* microsclerotium is prepared by the above solution.

In the present invention, the microsclerotium prepared by the above solution is mixed with a padding for drying to obtain a dried microsclerotium; in the present invention, the padding is one or more of diatomite, starch and cyclodextrin; the mass ratio of the microsclerotium to the padding is 1: (2-4), preferably 1:3; the drying mode is preferably hot air drying; the drying temperature is preferably 30-40° C., more preferably 32° C.; the drying time is preferably 24-48 h, more preferably 36 h. In the present invention, water content of the dried microsclerotium is preferably ≤8%.

In the present invention, the prepared dried microsclerotium is mixed with an auxiliary to obtain the microsclerotium formulation; the auxiliary is sucrose ester; the mass ratio of the dried microsclerotium to sucrose ester is 1000: 1-200:1, preferably 800:1-400:1, more preferably 600:1; the mixing mode is preferably stirring for mixing; the rotation speed of the mixing is 15-25 rpm, preferably 20 rpm; the stirring time is preferably 20-40 min, more preferably 30 min. In the present invention, the dosage form of the *Beauveria bassiana* microsclerotium formulation is granule.

The present invention provides an application of the *Beauveria bassiana* microsclerotium formulation prepared by the above solution in various peasts control. *Beauveria bassiana* is a kind of broad-spectrum pathogenic fungus and has good insecticidal activity to various kinds of *Lepidoptera*, Coleoptera and Hemiptera peasts, and it is widely applied in the biological control of various domestic and overseas pests, such as *agrotis* ypsilon and pine moth. In the present invention, the controlled pests are preferably grub, flatheaded borer, cutworm and Diptera larvae.

In the present invention, the application process of the *Beauveria bassiana* microsclerotium formulation is soil broadcasting, seed dressing or root irrigation mixed with water, preferably root irrigation mixed with water, the mixing ratio of the *Beauveria bassiana* microsclerotium formulation to water is 1:(200-1000), more preferably 1:500. In detailed implementation process of the present invention, the mixing ratio of the *Beauveria bassiana* microsclerotium formulation to water is determined according to the occurrence quantity and age of pests.

A preparation method of a *Beauveria bassiana* microsclerotium and formulation thereof, an application of the formulation thereof provided by the present invention will be described in detail with reference to embodiments below, but these embodiments should be construed as limiting the protection scope of the present invention.

Embodiment 1 a Preparation Method of *Beauveria bassiana* Microsclerotium

1) *Beauveria bassiana* Vuill strain with the accession number of CGMCC NO 15987 was inoculated into a PDA medium plate with 90 mm diameter for culture for 12 d at 23° C., conidia on the surface of the plate were scrapped after hyphae grow all over the plate and produce spores as initial inoculants.

2) The collected initial inoculants were added to 0.03% Tween® 20 sterile water (volume percent) for sterile operation and even dispersion to be prepared into a spore suspension with $3.0 \times 10^6$ spores/mL spore content for further use.

3) The prepared spore suspension was inoculated into a liquid induction medium by 1:20 volume ratio so that the final concentration of spores was up to $1.5 \times 10^5$ spores/mL, then put into a constant temperature shaker for culture. It was cultured for 6 d at 23° C., moreover, the rotation speed of the shaker after inoculation within 24 h was 50 rpm, and after 24 h, the rotation speed was regulated to 150 rpm, finally, the *Beauveria bassiana* microsclerotium was obtained by the above culture.

The liquid induction medium includes the following ingredients: counted by 1 L, basal salt: 2 g $KH_2PO_4$, 0.3 g $MgSO_4 \cdot 7H_2O$, 0.4 g $NaNO_3$, trace elements: 0.2 g $CuSO_4$, nitrogen source: 1.5 g yeast powder, 1 g peptone; carbon source: 10 g sucrose, 0.25 mL Tween® 20 and 1000 mL water, pH=6.0.

Embodiment 2 a Preparation Method of *Beauveria bassiana* Microsclerotium

1) *Beauveria bassiana* strain with the accession number of CGMCC NO 15987 was inoculated into a PDA solid medium plate with 90 mm diameter for culture for 10 d at 27° C., conidia on the surface of the plate were scrapped after hyphae grow all over the plate and produce spores as initial inoculants.

2) The collected initial inoculants were added to 0.1% Tween® 20 sterile water (volume percent) for sterile operation and even dispersion to be prepared into a spore suspension with $3.0 \times 10^6$ spores/mL spore content for further use.

3) The prepared spore suspension was inoculated into a liquid induction medium by 1:20 volume ratio so that the final concentration of spores was up to $1.5 \times 10^5$ spores/mL, then put into a constant temperature shaker for culture. It was cultured for 5.5 d at 31° C., moreover, the rotation speed of the shaker after inoculation within 24 h was 100 rpm, and after 24 h, the rotation speed was regulated to 200 rpm, finally, the *Beauveria bassiana* Vuill microsclerotium was obtained by the above culture.

The liquid induction medium includes the following ingredients: counted by 1 L, basal salt: 6 g $KH_2PO_4$, 0.9 g $MgSO_4 \cdot 7H_2O$, 1.2 g $NaNO_3$, trace elements: 0.6 g $CuSO_4$, nitrogen source: 4.5 g yeast powder, 3 g peptone; carbon source: 30 g sucrose, 0.75 mL Tween® 20 and 1000 mL water, pH=7.0.

Embodiment 3 a Preparation Method of *Beauveria bassiana* Microsclerotium

1) *Beauveria bassiana* strain with the accession number of CGMCC NO 15987 was inoculated into a PDA solid medium plate with 90 mm diameter for culture for 11 d at 25° C., conidia on the surface of the plate were scrapped after hyphae grow all over the plate and produce spores as initial inoculants.

2) The collected initial inoculants were added to 0.05% Tween® 20 sterile water (volume percent) for sterile operation and even dispersion to be prepared into a spore suspension with $3.0 \times 10^6$ spores/mL spore content for further use.

3) The prepared spore suspension was inoculated into a liquid induction medium by 1:15 volume ratio so that the final concentration of spores was up to $2.0 \times 10^5$ spores/mL, then put into a constant temperature shaker for culture. It was cultured for 5.5 d at 28° C., moreover, the rotation speed of the shaker after inoculation within 24 h was 50 rpm, and after 24 h, the rotation speed was regulated to 140 rpm, finally, the *Beauveria bassiana* microsclerotium was obtained by the above culture.

The liquid induction medium includes the following ingredients: counted by 1 L, basal salt: 6 g $KH_2PO_4$, 0.9 g $MgSO_4 \cdot 7H_2O$, 1.2 g $NaNO_3$, trace elements: 0.6 g $CuSO_4$, nitrogen source: 4.5 g yeast powder, 3 g peptone; carbon source: 30 g sucrose, 0.75 mL Tween® 20 and 1000 mL water, pH=7.2.

Embodiment 4 a Preparation Method of *Beauveria bassiana* Microsclerotium Formulation 1) The fermentation liquor of the *Beauveria bassiana* microsclerotium in Embodiment 3 was put into a 50 L plastic bucket, added corn starch which was 3 times of *Beauveria bassiana* microsclerotium by mass ratio for stirring evenly, added to a fluidized bed, then dried by hot air at 32° C. to water content≤8% to prepare dried microsclerotium.

The dried microsclerotium was added to sucrose ester according to 1000: 1 for stirring for 30 min to be prepared into microsclerotium granule.

Embodiment 5 a Preparation Method of *Beauveria bassiana* Microsclerotium Formulation 1) The fermentation liquor of the *Beauveria bassiana* microsclerotium in Embodiment 3 was put into a 50 L plastic bucket, added diatomite which was 4 times of *Beauveria bassiana* microsclerotium by mass ratio for stirring evenly, added to a fluidized bed, then dried by hot air at 35° C. to water content≤8% to prepare dried microsclerotium.

2) The dried microsclerotium was added to sucrose ester according to 800: 1 for stirring for 30 min to be prepared into microsclerotium granule.

Embodiment 6 Measurement on the Storage Tolerance of *Beauveria bassiana* Microsclerotium Formulation Obtained by Embodiment 5

Microsclerotium formulation obtained by Embodiment 5 was stored at room temperature (≤30° C.) in drying conditions, 0.05 g formulation were inoculated on a water agar plate every month to detect the germination rate of microsclerotium; it can be seen from the results that the rehydrated germination rate of the fungicide after drying is ≥99%, the rehydrated germination rate of the microsclerotium after stored for 12 months at room temperature is ≥95%.

TABLE 1

Germination rate of the *Beauveria bassiana* microsclerotium formulation after stored

| | Storage period Germination rate | | | | | | |
|---|---|---|---|---|---|---|---|
| | 0 month | 1 months | 3 months | 5 months | 7 months | 9 months | 12 months |
| Repetition 1 | 99% | 99% | 98% | 98% | 97% | 96% | 96% |
| Repetition 2 | 99% | 99% | 98% | 98% | 97% | 96% | 95% |
| Repetition 3 | 99% | 99% | 98% | 97% | 97% | 96% | 95% |

Embodiment 7 Test on the High Temperature Resistance of *Beauveria bassiana* Microsclerotium Formulation Obtained by Embodiment 5

0.02 g dried *Beauveria bassiana* microsclerotium obtained by Embodiment 5 were placed into a plastic centrifuge tube, and respectively processed for 0 min, 10 min, 20 min, 30 min at 35° C., 40° C., 45° C., 50° C., then taken out and respectively inoculated into a water agar plate medium for culture for 24 h at 25° C., thus measuring the germination rate of microsclerotium by an optical microscope. Meanwhile, fresh conidium spore suspension of $1 \times 10^7$ spores/mL was processed the same as the above as a control, all steps were repeated for 3 times.

It can be seen from Table 2 that for the treatment at 40° C. above, the germination rate of *Beauveria bassiana* microsclerotium is significantly higher than that of conidia under conditions of same temperature and processing time.

TABLE 2

Contrast of the germination rate of microsclerotium and conidium after heat treatment

| Temperature | | Germination rate (%) | | | |
| --- | --- | --- | --- | --- | --- |
| (° C.) | | 0 min | 10 min | 20 min | 30 min |
| 35 | Microsclerotium | 92.2 a | 91.6 a | 91.2 a | 91.3 a |
| | Conidium | 93.4 a | 92.6 a | 91.4 a | 91.1 a |
| 40 | Microsclerotium | 92.6 a | 92.0 a | 90.3 ab | 88.2 b |
| | Conidium | 93.3 a | 88.6 b | 82.4 c | 79.1 c |
| 45 | Microsclerotium | 92.3 a | 87.8 b | 70.4 d | 54.6 d |
| | Conidium | 92.8 a | 79.2 c | 55.4 e | 33.8 e |
| 50 | Microsclerotium | 92.4 a | 78.6 c | 57.5 e | 23.5 f |
| | Conidium | 93.1 a | 32.5 d | 13.5 f | 4.8 g |

Data in the table are average values after 3 repetitions, and different letters behind of the data in each list show significant difference (P<0.05).

Embodiment 8 Test on the UV Tolerance of Dried *Beauveria bassiana* Microsclerotium Obtained by Embodiment 5

0.02 g dried *Beauveria bassiana* microsclerotium obtained by Embodiment 5 were evenly smeared on a water agar plate with 9 cm diameter, and put into a 60 cm square of irradiation chamber and irradiated by a 40 W UV lamp (UV-B wavelength: 308), and the UV radiation quantity was measured by an ultraviolet spectrophotometer. It was irradiated for 0, 1, 2, 3, 4 h respectively, and the UV radiation quantity of each treatment was 0, 4.86, 9.72, 14.58 and 19.44 kJ $m^{-2}$. Microsclerotium was taken out of the irradiation chamber, put into a 25° C. incubator for cultivation for 24 h, then examined by an optical microscope to measure the germination rate of microsclerotium. Meanwhile, fresh conidium spore suspension of $1 \times 10^7$ *Beauveria bassiana* was processed the same as the above as a control, all steps were repeated for 3 times. The results are shown in the table below, it can be seen from the table that the germination rate of *Beauveria bassiana* microsclerotium is significantly higher than that of conidia under same dosage of UV irradiation.

TABLE 3

Test results of the microsclerotium UV tolerance

| UV-B exposure | Microsclerotium germination rate (%) | Conidium germination rate (%) |
| --- | --- | --- |
| 0 | 93.5 a | 92.9 a |
| 4.86 | 88.97 b | 75.27 c |
| 9.72 | 78.83 c | 62.23 d |
| 14.58 | 46.23 e | 31.07 f |
| 19.44 | 19.47 g | 12.24 h |

Data in the table are average values after 3 repetitions, and different letters behind of the data in each list show significant difference (P<0.05).

Embodiment 9 Test on the Control of *Delia antiqua* by the *Beauveria bassiana* Microsclerotium Formulation Obtained in Embodiment 5

Adult *Delia antiqua* was fed by sterile water, white granulated sugar and yeast powder in a 30×30×30 cm sarong, and then put into an automatically-controlled light and temperature incubator (23±1.0° C., LD16:8, 50-70% relative humidity). A 8 cm×5 cm-diameter plastic dish containing wet pebbles and pieces of onion was put to the sarong meanwhile for the nourishment supply and oviposition of the adult *Delia antiqua*. The ovi were incubated into larvae in the incubator under same conditions, and fed by sliced onion bulbs for further use.

3 small onion bulbs purchased from the market were respectively planted in each 40 cm-diameter plastic flowerpot, and inoculated with 20 3-day-old *Delia antiqua* larvae after the leaves of the onion grew to 10 cm in height. Then the inoculated flowerpots were put into an illumination incubator for routine culture (23±1.0° C., LD16:8, 50-70% relative humidity), the microsclerotium formulation obtained from step 5 was evenly mixed with water as inoculants according to a ratio of 1:20, and roots were irrigated by 100 mL inoculants per pot; and in a control group, roots were irrigated by fresh water. Survival number of *Delia antiqua* larvae in soil was respectively examined on the 5th and 10th day, and corrected mortality was calculated based upon a formula: corrected mortality (%)=(treatment mortality-control mortality)/(1-control mortality)×100%. All treatment was repeated for 10 times. Experiment results indicate that the corrected mortality of larvae 5 days later is 39.13% and it is up to 81.99% 10 days later; the dried larvae were put into a moist culture dish, 15 days later, it was be found that the *Delia antiqua* larvae were ossified, white hyphae and conidia grew on the surface of the majority of the polypides, indicating that *Delia antiqua* was infected to death by *Beauveria bassiana*. In the control group, there was a few of dead larvae, and no ossified larvae.

TABLE 4

Pot experiment on the control of *Delia antiqua* by *Beauveria bassiana* microsclerotium

| Number of the survival larvae | 0 d | 5 d | 10 d | 15 d |
| --- | --- | --- | --- | --- |
| Treatment | 200 | 98 | 29 | 13 |
| Control | 200 | 178 | 161 | 150 |
| Corrected mortality (%) | — | 35.75 | 81.99 | 91.4 |

It can be seen from the above embodiments that the present invention provides a *Beauveria bassiana* microsclerotium formulation and a preparation method of a formulation thereof; the *Beauveria bassiana* microsclerotium formulation prepared by the method has long shelf life at room temperature, high rehydration germination rate and has good effect in pest control.

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

What is claimed is:

1. A method for preparation of *Beauveria bassiana* microsclerotium, comprising the following steps of:
   1) mixing conidia of *Beauveria bassiana* with an aqueous solution comprising polyoxyethylene (20) sorbitan monolaurate to obtain a spore suspension; and
   2) inoculating the spore suspension obtained in step 1) into a liquid induction medium for induction culture to obtain the microsclerotium; wherein,
   the volume percent of polyoxyethylene (20) sorbitan monolaurate in the aqueous solution in step 1) is 0.03%-0.1%;
   with water as solvent, per liter of the liquid induction medium in step 2) having a pH of 6.0-7.5 comprises the following ingredients: 2-6 g $KH_2PO_4$, 0.3-0.9 g $MgSO_4 \cdot 7H_2O$, 0.4-1.2 g $NaNO3$, 0.2-0.6 g $CuSO_4$, 1.5-4.5 g yeast powder, 1-3 g peptone; 10-30 g sucrose, and 2.5 mL polyoxyethylene (20) sorbitan monolaurate;
   the *Beauveria bassiana* strain is CQBb119 and the accession number is CGMCC NO: 15987;
   the spore content of the spore suspension in step 1) is $2.8 \times 10^6$-$3.2 \times 10^6$ spores/mL;
   the volume ratio of the inoculated spore suspension in step 2) to the liquid induction medium is 1:10 to 1:20; and
   the induction culture temperature in step 2) is 23-31° C.; the induction culture time period is 5-6 days; and an oscillation or stirring frequency of the induction culture is 50-250 rpm.

2. A method for preparing a formulation comprising *Beauveria bassiana* microsclerotium, comprising the following steps of:
   A) mixing the microsclerotium prepared by the method as set forth in claim 1 with a padding for drying to obtain dried microsclerotium; and
   B) mixing the dried microsclerotium obtained in step A) with an auxiliary to obtain the microsclerotium formulation.

3. The method according to claim 2, wherein a dosage form of the microsclerotium formulation is granule.

4. The method according to claim 2, wherein the padding in step A) is one or more selected from the group consisting of diatomite, starch and cyclodextrin; and the volume ratio of the microsclerotium to the padding is 1:2 to 1:4.

5. The method according to claim 2, wherein the auxiliary in step B) is a sucrose ester; and the mass ratio of the dried microsclerotium to the sucrose ester is 1000:1-200:1.

* * * * *